US010189767B2

(12) United States Patent
Boit et al.

(10) Patent No.: US 10,189,767 B2
(45) Date of Patent: Jan. 29, 2019

(54) PROCESS FOR MANUFACTURING SUCCINIC ACID FROM A FERMENTATION BROTH USING NANO FILTRATION TO PURIFY RECYCLED MOTHER LIQUOR (71) Applicants: DSM IP ASSETS B.V., Heerlen (NL); ROQUETTE FRÈRES, Lestrem (FR)

(72) Inventors: Baptiste Boit, La Gorgue (FR); Guillaume Fiey, Dunkirk (FR); Maarten Job Van De Graaf, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/531,628

(22) PCT Filed: Dec. 1, 2015

(86) PCT No.: PCT/EP2015/078140
§ 371 (c)(1),
(2) Date: May 30, 2017

(87) PCT Pub. No.: WO2016/087408
PCT Pub. Date: Jun. 9, 2016

(65) Prior Publication Data
US 2017/0320805 A1 Nov. 9, 2017

(30) Foreign Application Priority Data
Dec. 2, 2014 (EP) .................................... 14306937

(51) Int. Cl.
*C07C 51/43* (2006.01)
*C07C 51/47* (2006.01)

(52) U.S. Cl.
CPC .............. *C07C 51/47* (2013.01); *C07C 51/43* (2013.01)

(58) Field of Classification Search
CPC .................................. C07C 55/10; C07C 51/42
See application file for complete search history.

(56) References Cited

U.S. PATENT DOCUMENTS

| | | | |
|---|---|---|---|
| 6,284,904 B1 | 9/2001 | Ponnampalam et al. | |
| 7,223,567 B2 | 5/2007 | Ka-Yiu et al. | |
| 2014/0349356 A1 | 11/2014 | Jiang et al. | |
| 2017/0217871 A1* | 8/2017 | Schutze | ................. C07C 51/43 |

FOREIGN PATENT DOCUMENTS

| | | | |
|---|---|---|---|
| CN | 101475464 B | * | 8/2011 |
| CN | 102942472 A | | 2/2013 |
| DE | 102013000027 A1 | | 7/2014 |
| EP | 1686182 A1 | | 8/2006 |
| EP | 2 371 802 A1 | | 5/2011 |
| EP | 2371804 A1 | | 10/2011 |
| EP | 2504307 A1 | | 10/2012 |
| EP | 2508501 A2 | | 10/2012 |
| JP | 2011219409 A | | 11/2011 |
| WO | 2006031424 A2 | | 3/2006 |
| WO | 2009065778 A1 | | 5/2009 |
| WO | 2009065780 A1 | | 5/2009 |
| WO | 2009083756 A1 | | 7/2009 |
| WO | 2011064151 A1 | | 6/2011 |
| WO | 2013039647 A1 | | 3/2013 |

OTHER PUBLICATIONS

Bowen et al, AIChE Journal, Diafiltration by Nanofiltration: Prediction and Optimization, 1998, 44(8), pp. 1799-1812. (Year: 1998).*
Baldea et al, IFAC Advanced Control of Chemical Processes, Dynamics of Process Networks with Recycle and Purge: Time Scale Separation and Model Decomposition, 2003, pp. 587-582. (Year: 2003).*
International Search Report of PCT/EP2015/078140 dated Feb. 1, 2016.
Sanchez, Ailen M. et al., "Novel pathway engineering design of the anaerobic central metabolic pathway in *Escherichia coli* to increase succinate yield and productivity", Metabolic Engineering, 2005, pp. 229-239, vol. 7.

* cited by examiner

Primary Examiner — Paul A Zucker
(74) Attorney, Agent, or Firm — McBee Moore Woodward & Vanik IP, LLC; Susan McBee; Chester Moore (57) ABSTRACT

A process for manufacturing succinic acid as obtained by fermentation is provided including crystallizing the succinic acid from an aqueous solution, separating the crystals from the mother liquor, treating the mother liquor by nanofiltration and recycling the treated mother liquor to the crystallization step. This process exhibits a high yield in terms of succinic acid crystals recovery and allowing to achieve a final product with a low content of saccharides.

16 Claims, 3 Drawing Sheets

PROCESS FOR MANUFACTURING SUCCINIC ACID FROM A FERMENTATION BROTH USING NANO FILTRATION TO PURIFY RECYCLED MOTHER LIQUOR

CROSS REFERENCE TO RELATED APPLICATIONS

This application claims the benefit of European Application No. EP14306937.5, filed 2 Dec. 2014, and PCT application No. PCT/EP2015/078140, filed 1 Dec. 2015.

BACKGROUND

Field of the Invention

It is the object of the present invention to provide a process for manufacturing succinic acid as obtained by fermentation, said process exhibiting a high yield in terms of succinic acid crystals recovery and allowing to achieve a final product with a low content of saccharides.

Description of Related Art

Succinic acid is a C4-dicarboxylic acid and is an intermediate of the tricarboxylic acid cycle (TCA). Global production of succinic acid is estimated at 16,000 to 30,000 tonnes a year, with an annual growth rate of 10%. Succinic acid finds numerous applications in the cosmetic, pharmaceutical, food industry and in the preparation of polymers. In the food and beverage industry, it is used as an acid regulator or pH controlling agent. In nutraceutical form as a food additive and dietary supplements, succinic acid is safe and approved by the U.S. Food and Drug Administration (FDA). As an excipient in pharmaceutical products it is used to control acidity and, more rarely, in effervescent tablets.

Succinic acid and its derivative diamines and diols can be used as monomer units of a variety of plastics, such as polyesters, polyamides, and polyester amides. Among them, poly(butylene succinate) (PBS) and its copolymers are a family of biodegradable polyesters synthesized from succinic acid, butanediol, or other dicarboxylates and alkyldiols. Owing to their excellent thermal processability, balanced mechanical properties, and good biodegradability, they have attracted intense attention from both academia and industry. PBS products can find wide applications as supermarket bags, packaging film, mulch film, and other disposable articles. It must be pointed out that PBS application of succinic acid requires a high degree of purity of said acid.

Thus far, succinic acid is predominantly produced via petrochemical processes including hydrogenation of maleic acid, oxidation of 1,4-butanediol, and carbonylation of ethylene glycol. However, this route is considered involving processes harmful to the environment. The production of succinic acid from renewable feedstocks—via the so-called biological production route via fermentation- has been focused on as an attractive alternative to petrochemical-based processes. This is an avenue to supplant the more energy intensive and more detrimental to the environment methods of deriving such acid from nonrenewable resources.

Methods of manufacturing succinic acid by fermentation involve basically crystallization of succinic acid from a fermentation broth and the further purification/recovery of succinic acid. From an industrial perspective, achieving a maximal yield in terms of succinic acid crystals recovery is of major importance. Several documents are disclosing for years some routes in order to increase said yield.

EP 2 371 802 discloses a process of crystallizing succinic acid, where an aqueous solution comprising succinic acid is treated with an oxidizing agent, said succinic acid being further crystallized. This method is very efficient in order to remove impurities such as fumaric and orotic acids and to reduce coloration in the final succinic acid crystals, without negatively impacting the global yield in terms of succinic acid crystals recovery. In a preferred embodiment, it is claimed that the mother liquor containing residual succinic acid and impurities, and resulting from the step of crystallization, can be recycled to the step of crystallization, thus allowing to increase the yield of succinic acid crystals produced. In a particular embodiment, the ozone treatment is applied on the mother liquor stream before recycling, in order to remove part of impurities and improve crystals quality.

EP 2 504 307 discloses a process for recovering succinic acid in crystal form from a fermentation broth. Said method comprises the steps of a) bringing the fermentation broth to a pH of between 1 and 4, b) crystallizing the succinic acid, c) dissolving the succinic acid crystals at a temperature ranging from 30 to 90° C., d) polishing and recrystallizing the succinic acid. Succinic acid crystals are obtained, comprising a sugar content of 1 to 100 ppm and a nitrogen content of 1 to 80 ppm. Furthermore, the mother liquor from step b) may be recycled to the feed of step b), said recycling step being found advantageous to increase the yield of succinic acid.

WO 2013/088239 discloses a process for removing color bodies from crude succinic acid, comprising distillation of crude succinic acid and collecting the distillate in a water-containing receiver. The color bodies substantially remain in the distillation bottoms and the purified succinic in the water-containing receiver is substantially free of color bodies. A backward loop can be implemented in order to recycle the distillation residue to the ammonia removal distillation step. Distillation with full recycles has essentially no loss of succinic acid and near quantitative recovery of contained succinic acid is possible.

EP 2 508 501 discloses a method for producing dicarboxylic acids such as succinic acid from fermentation derived solutions containing salts of succinic acid. Said method consists in providing fermentation derived diammonium succinate (DAS) containing solution, converting said solution to a solution containing a half-acid, half-salt of succinic acid (MXS) by reactive evaporation, crystallizing said solution by cooling and/or evaporative crystallization, converting MXS to succinic acid by biopolar membrane electrodialysis, anion exchange, cation exchange, or a combination thereof, and crystallizing succinic acid by cooling and/or evaporative crystallization. It is mentioned that succinic acid contained in the crystallization mother liquor may be recycled to the reactive evaporation step.

WO 2013/039647 discloses a process for the preparation of carboxylic acids like succinic acid (SA) from their corresponding biologically-produced ammonium salts (like DAS) and/or amides and/or imides. The process involves reacting the biologically-produced derivatives at high temperature, removing ammonia and water, crystallizing the carboxylic acid obtained and recycling the mother liquor to the reaction system. Near total recycle of crystallization mother liquor to the process is provided, which yields near quantitative conversion of the biologically produced ammonium carboxylates to the carboxylic acids.

EP 2 371 804 discloses a process for making succinic acid from a clarified diammonium succinate-containing fermentation broth comprising distilling the broth under super atmospheric pressure at a temperature ranging from 100 to 300° C., cooling and/or evaporating the bottoms that comprise succinic acid to separate said bottoms into a liquid portion and a solid portion substantially pure in succinic acid; and separating the solid portion from the liquid portion. The mother liquor from the solids separation step can be recycled to the distillation apparatus in order to enhance the recovery of succinic acid.

CN 102942472 discloses a method of extracting succinic acid from microorganism fermentation liquor. Initially, the succinate fermentation liquor is clarified, then acidized, subjected to reduced pressure distillation and to further cooling crystallization under stirring. The filter liquor obtained is concentrated while the residual mother liquor is subjected to cyclic operation, in order to obtain at least high-purity succinic acid crystals.

In view of the prior art, recycling the mother liquor resulting from the step of crystallization appears to be at least a possible embodiment of the general process and at best as an opportunity to increase the yield of said process. However, yield and purity are generally speaking dual concepts. This is emphasized in EP 2 371 802 that addresses the question of how to achieve a compromise between these 2 parameters.

As a matter of fact, purity is also a main issue dealing with the industrial production of succinic acid, especially in the case of production by fermentation. Such a route uses various bacteria: *Actinobacillus succinogenes*, *Mannheimia succiniciproducens* and *Escherichia coli*, as well as fungi such as *Aspergillus niger* and *Saccharomyces cerevisiae*. During the microbial fermentation numerous impurities like organic acids, proteins and the like are also produced. One has also to pay a particular attention to saccharides which are present in the raw material: they cannot be often totally consumed by the microorganism and will contaminate the organic acid to be produced. These and other impurities need to be removed upon recovery of succinic acid from the fermentation broth to obtain succinic acid crystals with a sufficiently high purity. As already mentioned, the use of succinic acid as a monomer for the preparation of PBS requires a high degree of purity of said acid.

Many documents have already addressed the problem of saccharide elimination during the production of succinic acid (or of another organic acid) via the fermentation route. U.S. Pat. No. 6,284,904 discloses a method for separating carboxylic acids from saccharide. The method involves removing impurities by allowing the anionic form of the carboxylic acid to bind to an anion exchange column and washing the column. The carboxylic anion is displaced as carboxylic acid by washing the resin with a strong inorganic anion. However, the corresponding operations for adsorption to the resin, recycle, and the like are complex, and the resin degrades by repeated recycle operations.

JP 2011 219409 discloses a method for producing an aliphatic dicarboxylic acid in a high purification degree by removing various materials originated from a biomass resource with the use of an activated carbon having a specific surface area ranging from 1500 to 5000 $m^2/g$. However, this method cannot be regarded as cheap, facing with the cost not only of the activated carbon but also of the non-recyclable consumable apparatus.

At least, EP 1 686 182 discloses a method of purification owing to the use of organic solvents. Said process comprises heating a mixture of organic acid salt and saccharide, contacting the heated mixture with alcohol, and then separating the organic acid salt from the heated saccharide. However, solvents may be harmful for the environment but also for people. At least, much energy must be consumed for solvent removal, and the cost is too excessive for separating small amounts of saccharide as impurities. Said document also points out that recrystallization or washing for obtaining a high purity organic acid decreases the recovery ratio of the organic acid. Meanwhile, recycling the organic acid for improving its recovery ratio has a problem that trace amounts of saccharide accumulate gradually.

In view of that, one has no choice but to note that there is no efficient process at that date for manufacturing succinic acid, preferably from a fermentation broth, in order to improve the yield of succinic acid crystals recovery and in order to simultaneously achieve a low sugar content into the final product.

SUMMARY

It is an object of the present invention to provide a process allowing to solve the above-mentioned technical problem. Said process comprises:
 a) providing an aqueous solution of succinic acid;
 b) crystallizing the succinic acid from the aqueous solution to form intermediate crystals and a mother liquor;
 c) separating the intermediate crystals from the mother liquor;
 d) treating the mother liquor by nanofiltration;
 e) recycling the treated mother liquor to step b);
 f) purifying the intermediate crystals; and
 g) recovering succinic acid.

DETAILED DESCRIPTION OF A PREFFERED EMBODIMENT

By selecting the mother liquor as the particular flux to be treated, the Applicant as shown that the yield of the process is improved, by comparison with the use of nano filtration in order to treat the main flux. It was not only non obvious to select the right stream to be treated, but EP 1 686 182 was also teaching away the skilled man in the art from the selection of the mother liquor, since said document is pointing out that "recycling the organic acid for improving its recovery ratio has a problem that trace amounts of saccharide accumulate gradually" as already discussed.

EP 2 371 802 was the sole document disclosing that the mother liquor could be a stream of interest for treatment, the corresponding treatment being carried out with the aid of ozone. However, the Applicant has shown in the present invention that said treatment was not so efficient in terms of saccharide reduction and process yield.

Surprisingly, the Applicant has shown that not only the yield of the process was increased with the method according to the invention, but also that the content of impurities, especially saccharides, was dramatically decreased, in comparison with the same process not involving the nano filtration method or involving ozone treatment. Thus, owing to the process according to the invention, it is now possible to achieve a compromise of major interest between a process exhibiting a high yield in terms of succinic acid crystals recovery and the obtention of a succinic acid of high purity where the content of saccharide has been largely decreased.

DETAILED DESCRIPTION OF THE INVENTION

The process according to the invention comprises:
a) providing an aqueous solution of succinic acid;
b) crystallizing the succinic acid from the aqueous solution to form intermediate crystals and a mother liquor;
c) separating the intermediate crystals from the mother liquor;
d) treating the mother liquor by nanofiltration;
e) recycling the treated mother liquor to step b);
f) purifying the intermediate crystals; and
g) recovering succinic acid.

Step a): Providing an Aqueous Solution of Succinic Acid

The first step of said process consists in providing an aqueous solution of succinic acid. Aqueous solution of succinic acid means basically a composition containing at least water and succinic acid in a dissolved form and/or in crystal form. The general concentration of succinic acid in said aqueous solution is typically ranging from 1 to 90% by weight.

In a preferred embodiment, said aqueous solution is a fermentation broth, obtained by fermenting a microbial cell which produces succinic acid. The fermentation broth may be any suitable broth allowing growth of a microbial cell and production of succinic acid. The fermentation broth comprises any suitable carbon source such as glucose, fructose, galactose, xylose, arabinose, sucrose, lactose, raffinose and glycerol.

Fermenting a microbial cell may be carried out under aerobic conditions, anaerobic conditions, micro-aerophilic or oxygen limited conditions, or a combination of these fermentation conditions, for instance as disclosed in WO2009/083756. An anaerobic fermentation process is herein defined as a fermentation process run in the absence of oxygen or in which substantially no oxygen is consumed, preferably less than 5, 2.5 or 1 mmol/L/h, and wherein organic molecules serve as both electron donor and electron acceptors.

The fermenting of a microbial cell may be carried out at any suitable pH between 1 and 9, depending on the microbial cell. In the event the microbial cell is a bacterial cell, the pH in the fermentation broth preferably is between 5 and 8, preferably between 5.5 and 7.5. Usually the pH of the bacterial fermentation broth is maintained at these values by adding neutralizing agents such as potassium- or sodium hydroxide, or ammonium. In the event the microbial cell is a fungal cell the pH in the fermentation broth may range between 1 and 7, preferably between 2 and 6, preferably between 2.5 and 5. During fermentation of a fungal cell the pH usually decreases to a pH of between 1 and 4, preferably between 2 and 3. A suitable temperature at which the fermenting of a microbial cell may be carried out in the process according to the present invention may be between 5 and 60° C., preferably between 10 and 50° C., more preferably between 15 and 40° C., more preferably between 20 and 30° C., depending on the microbial cell. The skilled man in the art knows the optimal temperatures for fermenting a microbial cell in the process of the invention.

In one embodiment, the microbial cell is a bacterium from the genus *Mannheimia*, *Anaerobiospirillum*, *Bacillus*, or *Escherichia*, or a fungal cell from the genus *Saccharomyces*, *Aspergillus*, *Penicillium*, *Pichia*, *Kluyveromyces*, *Yarrowia*, *Candida*, *Hansenula*, *Humicola*, *Torulaspora*, *Trichosporon*, *Brettanomyces*, *Rhizopus*, *Zygosaccharomyces*, *Pachysolen* or *Yamadazyma*. Preferably, a bacterial cell belongs to a species *Mannheimia succiniciproducens*, *Anaerobiospirillum succiniciproducens Bacillus amylophylus*, *B. ruminucola* and *E. coli*, preferably an *E. coli*. Preferably, a fungal cell belongs to a species *Saccharomyces cervisiae*, *Saccharomyces uvarum*, *Saccharomyces bayanus*, *Aspergillus niger*, *Penicillium chrysogenum*, *P. symplissicum*, *Pichia stipidis*, *Kluyveromyces marxianus*, *K. lactis*, *K. thermotolerans*, *Yarrowia lipolytica*, *Candida sonorensis*, *C. glabrata*, *Hansenula polymorpha*, *Torulaspora delbrueckii*, *Brettanomyces bruxellensis*, *Rhizopus orizae* or *Zygosaccharomyces bailiff*. Preferably, a fungal cell is a yeast, preferably a *Saccharomyces cerevisiae*.

The microbial cell according to the present invention may be any suitable wild-type organism, or a genetically modified microorganism. Suitable genetically modified *E. coli* cells are disclosed in Sanchez et al., Metabolic Engineering, 7 (2005) 229-239, WO 2006/031424, and U.S. Pat. No. 7,223,567. Suitable fungal cells are disclosed in WO 2009/065780 and WO 2009/065778.

Step b): Crystallizing the Succinic Acid from the Aqueous Solution

The second step of the process according to the present invention consists in crystallizing the succinic acid from the aqueous solution to form intermediate crystals and a mother liquor.

Crystallization may be carried out by any method known by the skilled person in the art. Preferably, said crystallization comprises evaporative crystallization. In such a case, the crystallization step comprises an evaporation phase, wherein the aqueous solution is concentrated by evaporating water at a temperature of between 50 and 90° C., preferably between 60 and 80° C., more preferably between 65 and 80° C., and a crystallization phase, wherein the concentrated aqueous solution is brought to a temperature of between 1 and 25° C. so that crystallization occurs. By doing this, succinic acid crystals are formed in the aqueous solution due to cooling.

In one preferred embodiment, the crystallization comprises bringing the aqueous solution to a pH of between 1 and 4, preferably between 1 and 3, preferably between 1 and 2 by any suitable method known in the art. Bringing an aqueous solution to a preferred pH value may be carried out by subjecting the aqueous solution to water-dissociation bipolar electrodialysis and/or by acidification using a cation exchange resin or by adding strong acid(s) directly in said solution.

Preferably, bringing an aqueous solution to a preferred pH value may be carried out by passing the aqueous solution containing succinic acid through a cation exchange resin in $H^+$ form. Cation exchange resin step is well known by skilled man of the art and consist in exchanging cations from the solution for $H^+$ from the resin. Thus, the pH of aqueous solution decreases and succinic acid is obtained in its dissociated form prior crystallization.

Step c): Separating the Intermediate Crystals from the Mother Liquor

The third step of the process according to the present invention consists in separating the intermediate crystals from the mother liquor.

The intermediate crystals obtained in step c) are typically separated from mother liquor by filtration or centrifugation, preferably by centrifugation. After the separation, two main streams are obtained:
 a wet cake containing intermediate crystals; and
 a mother liquor containing the liquid phases from the separation step.

Step d): Treating the Mother Liquor

The fourth step of the process according to the present invention consists in treating the mother liquor, containing impurities and residual amount of succinic acid, by nanofiltration.

Nanofiltration can be carried out with membranes exhibiting typically a cut-off point ranging from 10 to 1 000 Da, preferably from 100 to 500 Da, more preferably from 100 to 300 Da.

Several nanofiltration membranes could be used such as DL2540 from GE® or NF270-2540 from DOW®. The preferred membrane is DL2540 as manufactured by GE® as it exhibits a good compromise between succinic acid recovery yield, impacting the efficiency of the process, retention of impurities, impacting the quality of the end product, and permeation flux, impacting the cost of the process.

The operating conditions for nanofiltration are typically as followed:
 temperature of mother liquor is elevated to a range from 10 to 80° C., preferably from 30 to 60° C., more preferably 30 to 40° C.,
 pH of the mother liquor solution is unchanged and is between 1 and 2,
 transmembrane pressure is between 1 and 20 bar, preferably between 5 and 20 bar, more preferably 10 bar.

Nanofiltration may comprise advantageously a concentration phase and a diafiltration phase. During concentration phase, sugars, nitrogen and pigments are retained by the membrane. Some di-trivalent ions are also retained while most of the succinic acid passes through the membrane. As flux is decreasing as a function of mass concentration factor, targeted mass concentration factor (MCF) is from 1 to 5, preferably from 2 to 3 in order to limit membrane surface and water consumption during subsequent diafiltration phase.

When targeted mass concentration factor is reached, the diafiltration phase is applied by washing the retentate with demineralized water in order to recover succinic acid remaining in the retentate. The diafiltration phase is performed preferably in continuous mode, maintaining level in tank and mass concentration factor constant. The temperature of said demineralized water is equal to operational temperature during concentration phase in order to avoid temperature shock and improve diafiltration flux. This allows minimizing water consumption during succinic acid recovery. Diafiltration rate is between 0.2 to 2 kg water/kg initial mother liquor (feed), preferably from 0.5 to 1.5 kg water/kg initial mother liquor.

The Treated Mother Liquor

In a preferred embodiment, step d) comprises treating the mother liquor by microfiltration prior to nanofiltration, in order to remove any solids and colloids. The microfiltration preceding nanofiltration prevents from damaging the nanofiltration membranes and limits fouling of nanofiltration membranes. Typical cut-off point for microfiltration membranes is between 150 kDa and 0.8 µm, and is preferably around 0.1 µm such as Kerasep BW as manufactured by Novasep®. Microfiltration membrane can be organic or mineral; preferably microfiltration is performed with mineral (ceramic) membranes, which are more robust.

Microfiltration is well known by the skilled man in the art. Applied to mother liquor stream, operating conditions for microfiltration can be the following ones:
 temperature of the mother liquor is elevated to a range from 10 to 80° C., preferably from 40 to 80° C., more preferably 40 to 50° C.,
 pH of the mother liquor solution is unchanged and is between 1 and 2,
 transmembrane pressure is between 0.5 and 5 bar, preferably between 0.5 and 2 bar,
 targeted mass concentration factor is between 1 and 30, preferably between 10 and 25 and optionally followed by a diafiltration step in order to optimize recovery of succinic acid.

Step e): Recycling the Mother Liquor into the Crystallization Step b)

The fifth step of the process according to the present invention consists in recycling the treated mother liquor to the previous step b) of crystallizing the succinic acid.

When the crystallization of the aqueous solution of succinic acid is carried out by evaporative crystallization, the treated mother liquor is typically added to the aqueous solution prior to the evaporation phase.

Step f): Purifying the Intermediate Crystals

The sixth step of the process according to the present invention consists in purifying the intermediate crystals.

In a preferred embodiment, the intermediate crystals obtained in step c) are purified by dissolving the intermediate crystals in water and treating the dissolved intermediate crystals with activated carbon and/or with ionic exchange resins in order to remove other impurities (such as ionic species or residual organic acids) and any coloring promotors.

The step of dissolving the intermediate succinic acid crystals may be carried out at a temperature of between 30 and 90° C., preferably between 35 and 90° C., more preferably between 40 and 90° C. It was found advantageous to dissolve succinic acid crystals at high T ° C., since a higher amount of succinic acid is dissolved in a lower amount of water as compared to dissolving succinic acid at a temperature of below 40° C. It was found advantageous to limit water consumption in the process according to the present invention, since this reduces the amount of energy and steam required to evaporate said additional water during subsequent concentration step prior crystallization of dissolved succinic acid.

Preferably, the solution containing said dissolved succinic acid crystals is passed through a column filled with granular activated carbon. This step is well known by the skilled man in the art and can be done using CPG 1240 as manufactured by CECA® or Carbosorb 1240 as manufactured by Purolite® for instance. This treatment will allow removing nitrogen compounds and color promotors.

Preferably, the said treated solution is then passed through a column filled of cation exchange resin under $H^+$ form in order to remove cations traces, especially iron, coming from previous steps, including activated carbon treatment. Used resin can be C150 as manufactured by Purolite® or DOW88 as manufactured by DOW® for instance.

Preferably, the said treated solution is then passed through a column filled of anion exchange resin under $OH^-$ form in order to remove anions and last color promotors traces. Used resin can be FPA55 as manufactured by DOW® or S4528 as manufactured by Bayer® for instance.

Step g): Recovering Succinic Acid

The seventh step of the process according to the present invention consists in recovering succinic acid.

The recovery of succinic acid is typically carried out by recrystallization. The solution obtained after the purification step f) is concentrated and crystallized in same manner than in step b) resulting in high purity succinic acid crystals and a second mother liquor. The succinic acid crystals are separated from the second mother liquor typically by filtration or centrifugation, washed and dried. Second mother liquor stream thus obtained is advantageously recycled back into step b), advantageously after being treated by nanofiltration, optionally preceded by microfiltration, similarly to the step d) described above.

Obtained final product is perfectly white and its purity is very high. It is especially adapted for very strict application such as PBS production.

Figure 1:
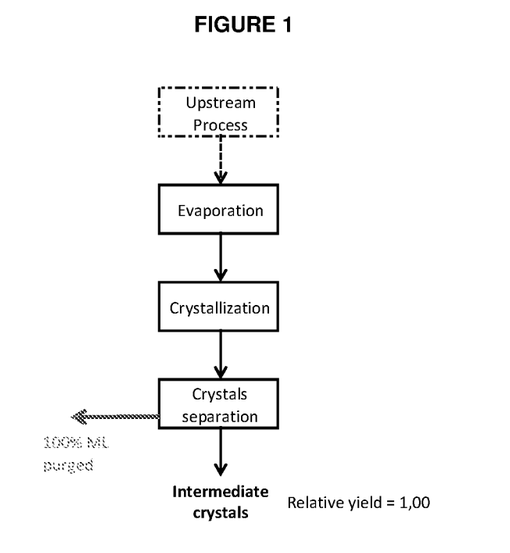
FIG. 1 is a scheme representing a process for manufacturing succinic acid without recycling mother liquor.

FIG. 1 illustrates a base case without mother liquor recycling. In this process, the entire mother liquor stream is purged. As a consequence, all succinic acid contained in this stream is lost and a big amount of effluent is sent to the waste water treatment plant, which has large economic and environmental impacts. In another hand, impurities (including sugars) contained in the mother liquor are not recycled within the crystallization step which allows reaching a good quality for the intermediate crystals, and for the final succinic acid consequently. The corresponding relative downstream process recovery yield for intermediate crystals is taken as reference for comparison with following cases and is set to 1.

Figure 2:
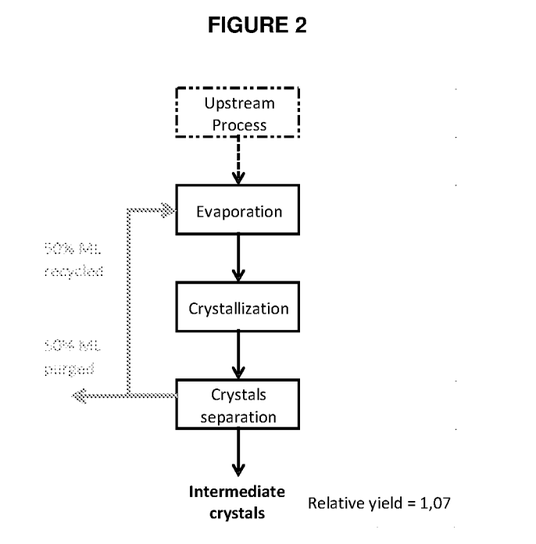
FIG. 2 is a scheme representing a process for manufacturing succinic acid with direct recycling of 50% of the mother liquor.

FIG. 2 illustrates a base case wherein 50% of mother liquor is recycled without any treatment. The amount of mother liquor sent to the waste water treatment plant is divided by two. This configuration is called base case with 50% mother liquor direct recycling. This process is advantageous for both economic and environmental aspects. As a result, part of succinic acid is also recovered via this recycle and the relative recovery yield is increased by 7%. On the other hand, impurities (including sugars) are also recycled and accumulated within crystallization step. This can impact the quality of intermediate crystals and potentially the quality of end product as well. The amount of succinic acid to be recovered via mother liquor recycle without treatment is thus limited by the impurities buildup effect that will impact quality.

Figure 3:
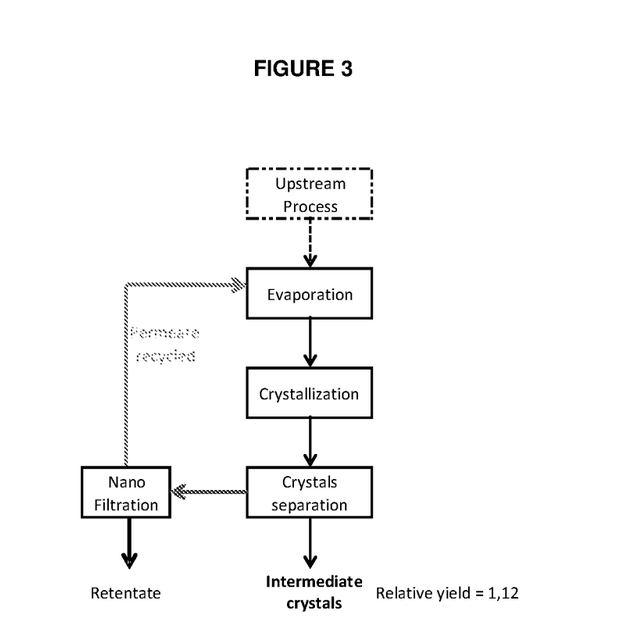
FIG. 3 is a scheme representing a process for manufacturing succinic acid with recycling of mother liquor after nanofiltration.

FIG. 3 illustrates a process according to the present invention wherein the mother liquor stream is treated by nanofiltration prior recycling back to the evaporation phase of the crystallization step b). When applying nanofiltration on the mother liquor stream before recycling, the effluent to be sent to the waste water treatment plant is the nanofiltration retentate, which is a small stream and represents a positive impact on cost and environment. The process according to the invention allows recovering succinic acid with a high yield and reasonable water consumption. 50 to 95% by weight, preferably from 70 to 95% by weight, more preferably from 80 to 95% by weight of succinic acid contained in the mother liquor is recovered in the treated mother liquor and recycled into the step b).

As a result, the relative recovery yield for the intermediate crystals is increased by 12%. In addition, during nanofiltration step, impurities (including sugars) are retained by the nanofiltration membrane while succinic acid is passing through. Consequently, purity of the mother liquor recycled back to the crystallization step b) after nanofiltration is much higher than in the base case with 50% mother liquor direct recycling (FIG. 2). As a result, there is no accumulation of impurities (including sugars) within the crystallization step and the product quality for the intermediate crystals is comparable with the base case without mother liquor recycle (FIG. 1).

Thus, treating mother liquor stream by nanofiltration prior recycle allows increasing the recovery yield of about 12% without impacting the quality of the intermediate crystals. In addition, amount of waste to be sent to the waste water treatment plant is also decreased.

EXAMPLES

Example 1

An aqueous solution containing succinic acid is obtained by fermentation, biomass separation and acidification using C150 cation exchange resin from Purolite®.

The fermentation broth is obtained as described in example 5.4 of the document WO 2011/064151. Acidification, crystallization and mother liquor recovery are performed as in example 5.5 of the same document.

Two main streams are thus obtained:
  a wet cake containing intermediate succinic acid crystals at high purity
  a mother liquor containing the liquid phases from the separation step.

Intermediate succinic acid crystals are then dissolved in demineralized water and the obtained solution is subsequently passed through columns filled with granular activated carbon (CPG1240) and cation (DOW88) and anion (S4528) exchange resins before final recrystallization.

Figure 4:
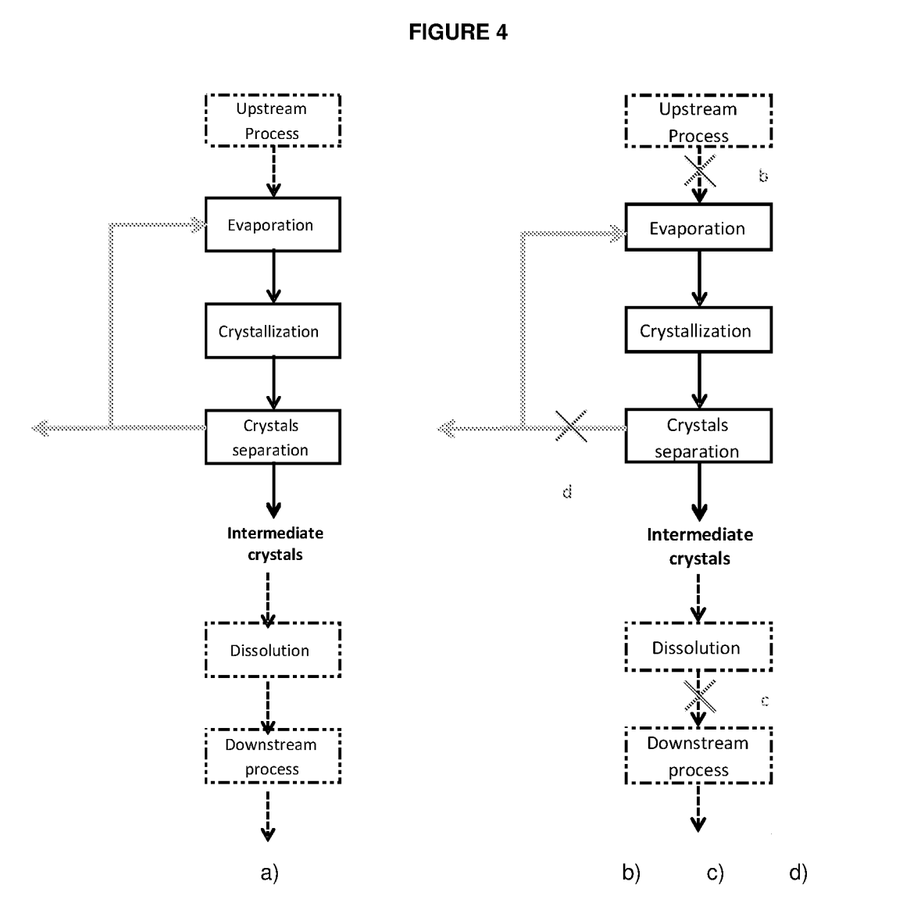
FIG. 4 is a scheme representing a process for manufacturing succinic acid with or without nanofiltration: a) base case with 50% mother liquor direct recycling, b) nanofiltration applied before crystallization, c) nanofiltration applied after dissolution, and d) nanofiltration applied on mother liquor before recycling (i.e. according to the invention).

This example is related to advantages of nanofiltration as a function of stream to be treated within downstream process. In FIG. 4, base case without nanofiltration (a) is compared to three other cases (b, c and d) where different streams are treated by nanofiltration. Location of nanofiltration unit within downstream process is indicated by crosses: case b) nanofiltration applied on the main stream before crystallization, case c) nanofiltration applied on the main stream after dissolution, and case d) nanofiltration applied on mother liquor before recycling (i.e. according to the invention).

A step of microfiltration is performed in order to remove any solids or colloids from the solution prior to nanofiltration. Microfiltration is performed in batch mode with a pilot skid as manufactured by TAMI®: permeate is recovered in a separated tank while retentate is recycled back to feed tank during concentration phase. The skid is equipped with Kerasep BW ceramic membrane from Novasep®; at 40° C. and a transmembrane pressure of 1. Initial solution is slightly turbid and obtained permeate is perfectly clear and ready to be treated by nanofiltration.

Nanofiltration is performed in pilot skid as manufactured by TIA®. It is performed in batch mode at 10 bar and 40° C. with DL2540 membrane from GE®: permeate is recovered in a separated tank while retentate is recycled back to feed tank during concentration phase. Permeation flux decreases gradually during concentration step and when it reaches 5 kg/h/m$^2$, mass concentration factor is recorded and diafiltration phase is then started by continuously adding demineralized water at 40° C. in feed tank while maintaining the level constant. Amount of added water and saccharide content (Brix) are monitored during diafiltration phase. When Brix of permeate (diafiltrate) is below 0.2 unit; diafiltration is stopped.

Depending on stream to be treated by nanofiltration, equipment size (and investment), impact on succinic acid recovery yield and water consumption will be different. The following table shows that regarding these criteria, the best stream to treat by nanofiltration is mother liquor stream. Indeed, compared to cases where main stream is treated (cases b and c), treating a secondary stream such as mother liquor (case d) leads to the highest succinic acid recovery yield for intermediate crystals and end product consequently with the smallest equipment size and the lowest water consumption.

TABLE 1

|  |  | Base case without recycle | Base case with 50% mother liquor direct recycle (a) | Nanofiltration on main stream | | Nanofiltration on secondary stream On mother Liquor (d) |
| --- | --- | --- | --- | --- | --- | --- |
|  |  |  |  | Before crystallization (b) | After dissolution (c) |  |
| Stream flowrate | Kg/h | — | — | 10000 | 7000 | 2000 |
| Permeation Flux | Kg/h/m² | — | — | 45 | 45 | 25 |
| Mass Concentration Factor | [ ] | — | — | 9 | 9 | 2.5 |
| Water consumption for dialiltration | Kg/h | — | — | 5000 | 3500 | 2000 |
| Nanofiltration surface (including washing) | Installed m² | — | — | 590 | 366 | 210 |
| Succinic acid recovery yield after nanofiltration | % | — | — | 99 | 99 | 90 |
| Succinic acid recovery yield in end product | Related to base case | 1.00 | 1.07 | 1.06 | 1.06 | 1.12 |

From table 1, it appears that for the base case without mother liquor (represented in FIG. 1): no mother liquor is recycled and no nanofiltration is performed. Recovery yield is set to 1.00 and used as reference for comparison.

For the base case with 50% mother liquor direct recycling: 50% (w/w) of the mother liquor stream is directly recycled back to previous evaporation step, without treatment. The corresponding amount of succinic acid recycled back to evaporation step is 50% (w/w) as well. Nanofiltration is not applied so no need for membranes and no additional water consumption for diafiltration. Relatively to base case without recycle, recovery yield for the end product is 1.07.

Facing with the cases where nanofiltration is applied on main stream : nanofiltration fluxes are high as main streams are relatively clean. However, main stream flow rates are high as well, which leads to significant membrane surfaces in order to treat the entire stream. In addition, a significant amount of additional water is needed to increase recovery yield of succinic acid during diafiltration step. This extra dilution will negatively impact steam and energy consumption needed in subsequent concentration step prior to crystallization. In addition, even in these conditions, some succinic acid remains in the retentate after diafiltration which results in an overall recovery yield for succinic acid in the end product, which is slightly lower than in the base case, around 1.06.

As regards to the case where nanofiltration is applied on the mother liquor: the entire mother liquor stream is treated by nanofiltration and diafiltration before recycling permeate and diafiltrate back to evaporation step. Nanofiltration flux on mother liquor is lower than on main stream as mother liquor contains more impurities than main streams. However, mother liquor stream is much lower than for the main streams, which finally leads to the smallest membrane surface needed for the operation. Consumption of additional water for diafiltration is also reduced compared to previous cases b and c. Extra dilution and impact on steam and energy consumption for evaporation step is then limited. In these conditions, succinic acid recovery yield after diafiltration step is 90%. Compared to the base case where 50% (w/w) of succinic acid is recycled with mother liquor stream without treatment, after performing nanofiltration on mother liquor, 90% of succinic acid contained in the mother liquor can be recycled. This leads to a recovery yield improvement, overall recovery yield for end product is 1.12.

As illustrated, applying nanofiltration on mother liquor instead of main stream allows to achieve the best impact on succinic acid recovery yield with the lowest additional water consumption and the smallest equipment size (lowest membrane surface).

Example 2

In this example, 2 different organic membranes are compared: DL2540 from GE® and NF270-2540 from DOW®.

Mother liquor stream is produced following the same protocol as in example 1. As in example 1, a step of microfiltration is performed on mother liquor stream prior nanofiltration in order to remove any colloids and solids in suspension.

After microfiltration, mother liquor is split in two parts:
  46.2 kg are used for nanofiltration trial with DL2540 organic membrane
  45.0 kg are used for nanofiltration trial with NF270-2540 organic membrane In both trials, microfiltrated mother liquor is introduced in feed tank of the TIA® nanofiltration skid, equipped either with DL2540 or NF270-2540 organic membranes and cleaned. Nanofiltration (including concentration phase and diafiltration phase) is performed in batch mode, temperature of feed tank is maintained at 40° C. thanks to a heat coil and operating pressure is 10 bar.

The table 2 below illustrates analytical results of mother liquor before and the treated mother liquor after nanofiltration on DL2540 membrane (>96% MgSO₄ rejection rate) from GE®.

TABLE 2

|  | Unit | Feed material (mother liquor after microfiltration) | Nanofiltration retentate | Treated mother liquor |
|---|---|---|---|---|
| Average permeation flux | Kg/h/m$^2$ | 25 | | |
| Weight | kg | 46.2 | 18.7 | 71.5 |
| Coloration | ICUMSA | 5665 | 17518 | 619 |
| Succinic acid | g/kg | 77.6 | 7.9 | 45.8 |
| Sugars | g/kg | 15.7 | 35.6 | 0.4 |
| Calcium | ppm | 8 | 10 | 2 |
| Iron | ppm | 4 | 8 | 0 |
| Sulfur | ppm | 377 | 218 | 172 |
| Total Nitrogen | ppm | 201 | 296 | 41 |

Color Measurement

The color in solution is measured at 420 nm in a spectrophotometer UVIKON 923 from Bio-Tek KONTRON. Coloration is expressed in ICUMSA unit (International Commission for Uniform Methods of Sugar Analysis), which was calculated as:

ICUMSA=(Abs 420$_{nm}$×100000)/Brix

One degree Brix (1° Brix), as measured with a refractometer, is equal to 1 g Saccharose in 100 g of solution at 20° C.

Determination of Sulphur and Cations

Sulphur and cations are determined by atomic emission spectrometry using inductively coupled plasma.

Determination of Anions

Anions such as sulfate, chloride and phosphate were separated on an anion exchange column, Dionex AS11-HC type, which was heated at 36 degrees Celsius, and detected by conductimetry. The eluent was a gradient of progressively increasing NaOH concentration. Trifluoroacetic acid (TFA) was used as internal standard.

Determination of Organic Acids

Organic acids were separated with ion exchange chromatography on columns (3 in series) from Biorad HPX-87H type, which were heated at 85 degrees Celsius and detected with UV at 210 nm. The elution solvent was a 5 mM sulphuric acid solution. The quantitative analysis was performed by external calibration. Pyruvic, malic, fumaric, lactic, formic and acetic acids were used as standards. The chromatographic separation was conducted in isocratic mode 60 microliters of a 3% succinic acid solution were injected.

Determination of Sugars

Sugars are analyzed after hydrolysis following the protocol below:

To 500 μl sample 500 μl 8N TFA is added to perform the hydrolysis for 4 hours at 100° C. Then the sample is lyophilized to remove the TFA and the residue is dissolved in 1500 μl Milli-Q water. If needed, the solution is diluted to a concentration of approximately 10 mg/l with Milli-Q water prior to injection to HPAEC system.

Results in table 2 show an averaged permeation flux of 25 kg/h/m$^2$ and that DL2540 nanofiltration membrane is able to remove more than 80% of coloration, more than 95% of sugars and a significant part of nitrogen and sulfur. This while reaching a succinic acid recovery yield higher than 90%.

Same experiment is performed with 45.0 kg of microfiltrated mother liquor on NF270-2540 membrane from DOW® (>97% MgSO$_4$ rejection rate). Results are as in table 3 below.

TABLE 3

|  | Unit | Feed material (mother liquor after microfiltration) | Nanofiltration retentate | Treated mother liquor |
|---|---|---|---|---|
| Average permeation flux | Kg/h/m$^2$ | 11 | | |
| Weight | kg | 45.0 | 16.8 | 62.5 |
| Coloration | ICUMSA | 5858 | 12337 | 285 |
| Succinic acid | g/kg | 77.9 | 15.6 | 45.4 |
| Sugars | g/kg | 12.9 | 39.5 | 0.1 |
| Calcium | ppm | 7 | 8 | 2 |
| Iron | ppm | 4 | 8 | 0 |
| Sulfur | ppm | 386 | 119 | 221 |
| Total Nitrogen | ppm | 200 | 400 | 29 |

Results in table 3 show that, compared to DL2540 membrane, NF270 membrane is able to remove more impurities, especially coloration, sugars and nitrogen. However, NF270 membrane also retains more succinic acid which leads to a lower succinic acid recovery yield.

In addition, permeation flux obtained with NF270 is twice lower than with DL2540 membrane, which means that twice the surface would be necessary to treat a same stream. Interest of using NF270 instead of DL2540 could be thus limited.

These observations are in line with rejection rate expressed by suppliers: the higher the rejection rate, the higher the amount of succinic acid retained on membrane. Between DL2540 and NF270 membranes, preferred membrane is DL2540 membrane as manufactured by GE®.

Example 3

Example 3 illustrates additional advantages of treating mother liquor by nanofiltration (with DL2540 membrane) in terms of quality and amount of waste water.

Three cases are compared:
Base case without mother liquor recycle
Base case with 50% (w/w) mother liquor direct recycle
Nanofiltration is applied on mother liquor before recycle The table below summarizes the results obtained for the three different cases:

TABLE 4

|  |  | Base case without recycle | Base case with 50% mother liquor direct recycle | Nanofiltration on mother liquor before recycle |
|---|---|---|---|---|
| Succinic acid recycled from mother liquor | % (w/w) | 0 | 50 | 90 |
| Sugars concentration within crystallization step | g/kg slurry | 19.5 | 36.7 | 18.3 |
| Effluent to waste water treatment plant | kg DM/h (kg/h) | 177 (1303) | 135 (692) | 96 (812) |
| Succinic acid recovery yield in end product | Related to base case | 1.00 | 1.07 | 1.12 |

Dealing with the base case without mother liquor recycle: as previously used, succinic acid recovery yield is set to 1 and is taken as reference for comparison. In that case, the entire mother liquor stream is purged: 1.3 t/h mother liquor, containing 177 kg of dry matter, are sent to the waste water treatment plant. This represents an additional cost for waste water treatment plant but allows crystallizing intermediate crystals in presence of relatively low level of sugars: 19.5 g/kg.

Concerning the base case with 50% direct mother liquor recycle: recycling 50% of mother liquor back to evaporation step allows increasing relative succinic acid recovery yield to 1.07 and reducing the amount of mother liquor to send to the waste water treatment plant: 0.7 t/h mother liquor, containing 135 kg of dry matter. However, dry matter content remains relatively high due to built-up of impurities during continuous production. For the same reason, major drawback of recycling 50% mother liquor directly without treatment is that, at steady state, crystallization of intermediate crystals then occurs in presence of relatively high level of sugars: 36.7 g/kg. This can negatively impact quality of intermediate crystals and final product.

Nanofiltration on mother liquor before recycle: as illustrated in example 2, performing nanofiltration and diafiltration on mother liquor with DL2540 membrane allows recovering 90% of succinic acid which leads to an increase of relative recovery yield up to 1.12. In parallel, as in that case the purge is the retentate after diafiltration, the amount of waste water to send to waste water treatment plant is also significantly reduced: 0.8 t/h of retentate containing 96 kg of dry matter. In addition, as the nanofiltration membrane retains 95% of sugars, recycling mother liquor after nanofiltration also allows crystallizing intermediate crystals in presence of a level of sugars comparable to base case without mother liquor recycle: 18.3 g/kg. In this configuration, quality of intermediate crystals is comparable with quality of intermediate crystals in base case without recycle.

Thus, applying nanofiltration on mother liquor before recycle allows producing same quality of intermediate crystals with an increased recovery yield of 12% and a reduced impact on waste water treatment (more than 40%).

Example 4

This example illustrates benefits of applying nanofiltration on mother liquor before recycle instead of ozone treatment before recycle. Results obtained in example 2 with DL2540 membrane are compared with results obtained after ozone treatment.

Ozone treatment is performed in batch mode as followed:
50 L of mother liquor are introduced in an agitated tank,
The tank is connected to a CFS06 OZONIA reactor which generates ozone,
Ozone flow rate injected in tank containing the mother liquor is fixed at 450 g/h,
Color reduction (ICUMSA) is followed until stabilization,
When residual coloration is stable, the treated mother liquor is analyzed.

TABLE 5

|  | Unit | Initial mother liquor | Ozone treatment | Nanofiltration |
|---|---|---|---|---|
| Color | ICUMSA | 5665 | 3222 | 619 |
| Color removal | % | — | 55 | >80 |
| Total nitrogen removal | % | — | 2 | >65 |
| Sugars removal | % | — | 6 | >95 |
| Succinic acid purity | %/DM | 77 | 77 | 88 |

Results show that ozone treatment is less efficient than nanofiltration regarding color, nitrogen and sugars removal. In addition, ozone treatment oxidizes these impurities but most of obtained products remain within the mother liquor.

As a result, purity of mother liquor treated with ozone is unchanged, whereas nanofiltration membrane physically retains impurities and significantly increases the purity of the mother liquor (from 77 to 88%/DM).

Thus nanofiltration is more efficient than ozone treatment to remove sugars, nitrogen and to increase purity of treated solution.

The invention claimed is:

1. A process for manufacturing succinic acid comprising:
   a) providing an aqueous solution of succinic acid;
   b) crystallizing the succinic acid from the aqueous solution to form intermediate crystals and a mother liquor;
   c) separating the intermediate crystals from the mother liquor;
   d) treating the mother liquor by nanofiltration;
   e) recycling the treated mother liquor to b);
   f) purifying the intermediate crystals; and
   g) recovering succinic acid.

2. A process according to claim 1, wherein the aqueous solution is a fermentation broth.

3. A process according to claim 1, wherein from 50 to 95% by weight of succinic acid contained in the mother liquor are recovered in the treated mother liquor and recycled into b).

4. A process according to claim 1, wherein nanofiltration is carried out with the use of filtration membrane exhibiting a cutoff point ranging from 10 to 1000 Da.

5. A process according to claim 4, wherein nanofiltration is carried out with the use of filtration membrane exhibiting a cutoff point ranging from 100 to 500 Da.

6. A process according to claim 1, wherein nanofiltration comprises a concentration phase and a diafiltration phase.

7. A process according to claim 1, wherein during the nanofiltration the temperature is ranging from 10 to 80° C.

8. A process according to claim 1, wherein during the nanofiltration the transmembrane pressure is between 1 and 20 bar.

9. A process according to claim 1, wherein the purification step f) comprises dissolving the intermediate crystals obtained in b) and treating the dissolved intermediate crystals with activated carbon and/or with ionic exchange resins.

10. A process according to claim 1, wherein the recovery step g) comprises recrystallizing the succinic acid obtained after purification step f).

11. A process according to claim 1, wherein from 70 to 95% by weight of succinic acid contained in the mother liquor are recovered in the treated mother liquor and recycled into b).

12. A process according to claim 1, wherein from 80 to 95% by weight of succinic acid contained in the mother liquor are recovered in the treated mother liquor and recycled into b).

13. A process according to claim 1, wherein nanofiltration is carried out with the use of filtration membrane exhibiting a cutoff point ranging from 100 to 300 Da.

14. A process according to claim 1, wherein during the nanofiltration the temperature is ranging from 30 to 50° C.

15. A process according to claim 1, wherein during the nanofiltration the transmembrane pressure is between 5 and 20 bar.

16. A process according to claim 1, wherein b) comprises bringing the aqueous solution of succinic acid to a pH of between 1 and 4.

* * * * *

UNITED STATES PATENT AND TRADEMARK OFFICE
CERTIFICATE OF CORRECTION

PATENT NO. : 10,189,767 B2  
APPLICATION NO. : 15/531628  
DATED : January 29, 2019  
INVENTOR(S) : Baptiste Boit, Guillaume Fiey and Maarten Job Van De Graaf Page 1 of 1

It is certified that error appears in the above-identified patent and that said Letters Patent is hereby corrected as shown below:

On the Title Page

Item (73) should be corrected to read:

| NAME | CITY | COUNTRY | CATEGORY |
|---|---|---|---|
| 1. DSM IP ASSETS B.V. | Heerlen | Netherlands | corporation |
| 2. ROQUETTE FRERES | Lestrem | France | corporation |

Signed and Sealed this  
Thirtieth Day of July, 2019

Andrei Iancu  
*Director of the United States Patent and Trademark Office*